United States Patent [19]
Ahmed

[11] Patent Number: 5,965,123
[45] Date of Patent: Oct. 12, 1999

[54] COATED PESTICIDAL AGENTS, PROCESSES FOR THEIR PREPARATION AND COMPOSITIONS CONTAINING THEM

[75] Inventor: Fakhruddin Ahmed, Princeton Junction, N.J.

[73] Assignee: American Cyanamid Company, Madison, N.J.

[21] Appl. No.: 08/322,679

[22] Filed: Oct. 13, 1994

Related U.S. Application Data

[63] Continuation-in-part of application No. 08/281,916, Jul. 27, 1994, Pat. No. 5,662,897.

[51] Int. Cl.⁶ .......................... A01N 63/00; A01N 25/26; A01N 25/28; A61K 37/00
[52] U.S. Cl. .................. 424/93.2; 424/93.6; 424/419
[58] Field of Search ................ 424/419, 93.6, 424/93.2, 405, 407, 409, 417, 487; 514/256; 428/403, 402.24; 427/2.21, 213.3, 213.34, 213.36; 523/122

[56] References Cited

U.S. PATENT DOCUMENTS

| | | | |
|---|---|---|---|
| 3,541,203 | 11/1970 | Fogle et al. | 435/235.1 |
| 4,844,896 | 7/1989 | Bohm et al. | 424/93.461 |
| 4,857,335 | 8/1989 | Bohm | 424/455 |
| 4,874,811 | 10/1989 | Borchers et al. | 524/516 |
| 4,894,240 | 1/1990 | Geoghegan et al. | 424/497 |
| 4,948,586 | 8/1990 | Bohm et al. | 424/406 |
| 4,981,693 | 1/1991 | Higashi et al. | 424/435 |
| 5,075,058 | 12/1991 | Chan et al. | 264/118 |
| 5,124,149 | 6/1992 | Shapiro et al. | 424/936 |
| 5,187,185 | 2/1993 | Treacy et al. | 514/408 |
| 5,225,443 | 7/1993 | Murphy et al. | 514/615 |
| 5,246,936 | 9/1993 | Treacy et al. | 514/256 |
| 5,462,915 | 10/1995 | Curtis et al. | 504/323 |
| 5,560,909 | 10/1996 | Rheaume et al. | 424/93.1 |

OTHER PUBLICATIONS 294,068. Oct. 1988. RD. Anonymous.

Primary Examiner—Karen Cochrane Carlson
Attorney, Agent, or Firm—Joseph M. Mazzarese

[57] ABSTRACT

The present invention provides a coated pesticidal agent and processes for its preparation. The present invention also provides a wettable powder pesticidal composition containing the coated pesticidal agent.

24 Claims, 6 Drawing Sheets

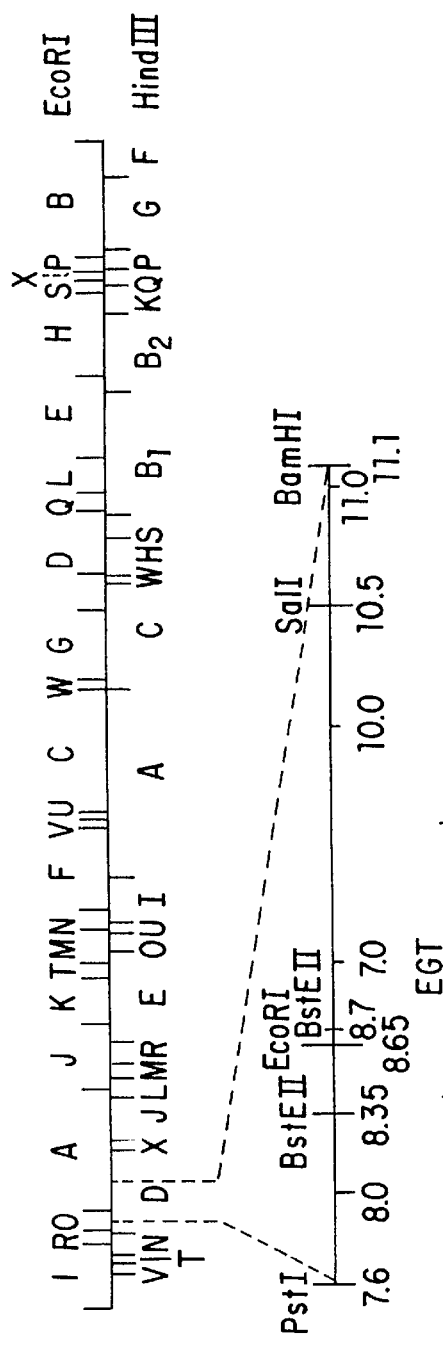
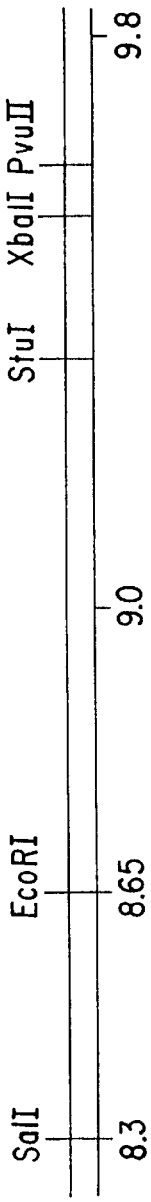
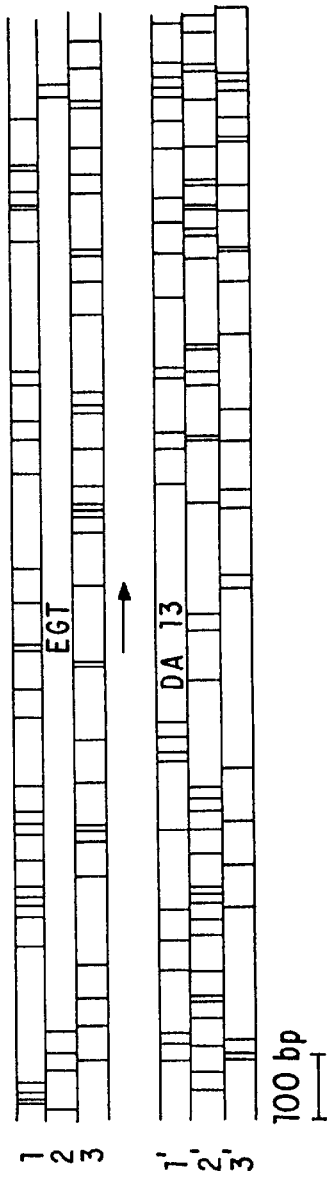
FIG. 1A
FIG. 1B
FIG. 2A
FIG. 2B

```
                          SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

CCTCAGGGCA GCTGCCTGCA GG                                                22

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

GCTCTGACGC ATTTCTACAA CCACGACTCC                                        30
```

(2) INFORMATION FOR SEQ ID NO:3:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
TAATCCTGCA GGCAGCTGCC CTGAGGATCA GCAACTATAT ATTAAGCCG          49
```

(2) INFORMATION FOR SEQ ID NO:4:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
GCTGCCTGCA GGATTATGTA AATAATTAAA ATGATAACCA TCTCGC             46
```

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

```
GGATTTCCTT GAAGAGAGTG AG                                       22
```

(2) INFORMATION FOR SEQ ID NO:6:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

```
AGCCCCCGAG TGCCTGCTCT CGAACTATTG CAACAATGAA TGCACCAAGG TGCACTACGC   60
TGACAAGGGC TACTGTTGCC TTCTGTCCTG CTATTGCTTC                        100
```

(2) INFORMATION FOR SEQ ID NO:7:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

```
CTGTAGGTAC CGGATCCTTA GTTAATGATG GTGGTGTCAC AGTAGCTCTT GCGAGTATCA      60

GAGATTTCCA GAACTTTCTT GTCGTCGTTG AGACCGAAGC AATAGCAGGA                110
```

(2) INFORMATION FOR SEQ ID NO:8:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

```
AGGCACTCGG GGGCTTTTCC GGATGAGGTC GACTGCGTAG CCGTTCTTCT T              51
```

(2) INFORMATION FOR SEQ ID NO:9:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

```
CCCCCCGGAT CCATGTACAA ACTGACCGTC TTCCTGATGT TCATCGCCTT CGTGATTATC      60

GCTGAGGCCA AGAAGAACGG CTAC                                            84
```

(2) INFORMATION FOR SEQ ID NO:10:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

```
CCCCCCGGAT CCATGTTCAA GTTCGTGATG ATCTGCGCCG TCCTCGGCCT GGCTGTGGCC      60

AAGAAGAACG GCTAC                                                      75
```

-continued (2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

```
ATGTACAAAC TGACCGTCTT CCTGATG                                    27
```

COATED PESTICIDAL AGENTS, PROCESSES FOR THEIR PREPARATION AND COMPOSITIONS CONTAINING THEM This application is a continuation-in-part of U.S. application Ser. No. 08/281,916 filed Jul. 27, 1994 entitled Insect Viruses, Sequences, Insecticidal Compositions and Methods of Use, now U.S. Pat. No. 5,662,897.

BACKGROUND OF THE INVENTION

Certain pesticidal agents are inactivated by ultraviolet radiation from the sun. Because those pesticidal agents are useful for the control of undesirable pests and are applied in areas where they will be exposed to ultraviolet radiation, there is a need for photostable compositions containing those agents.

To prevent ultraviolet inactivation of pesticidal agents, compositions have been prepared which contain ultraviolet absorbers and/or reflectors and a pesticidal agent.

U.S. Pat. No. 3,541,203 describes a protected virus composition for insect control. The preferred composition includes a virus, an actinic light absorbing material and a polymeric binder material. The patent discloses that to bind the admixture of an actinic light absorbing material and a virus together with an ethylcellulose polymeric material, the admixture is combined with an ethylcellulose in toluene solution. The resultant mixture is agitated, treated with polybutadiene and poured into petroleum distillate which causes the ethylcellulose to solidify to yield very small particles of ethylcellulose polymeric material having substantially homogeneously enclosed within the particles the admixture of the actinic light absorbing material and the virus. The particles are then washed several times with additional petroleum distillate to completely remove residual amounts of the liquid polybutadiene material. Unfortunately, the process used to prepare the preferred compositions of U.S. Pat. No. 3,541,203 is not entirely satisfactory because it requires the use of toxic materials and numerous washing steps with flammable solvents.

U.S. Pat. No. 4,948,586 discloses a microencapsulated insecticidal pathogen. Four microencapsulated compositions are shown to decrease the photoinactivation of *Autographa californica* NPV. However, the microencapsulated compositions only retained from 30.7 to 71.43% of the original activity before being exposed to sunlight. U.S. Pat. No. 4,948,586 discloses a method of preparing microencapsulated insecticidal pathogens which has numerous steps and is both time consuming and laborious. It is apparent that neither the process nor the microencapsulated insecticidal pathogens described in U.S. Pat. No. 4,948,586 are entirely satisfactory for protecting insecticidal pathogens from the effects of ultraviolet radiation.

It is an object of the present invention to provide a coated pesticidal agent which retains a significant amount of its original activity after exposure to ultraviolet radiation.

It is also an object of the present invention to provide simple, less arduous processes for the preparation of coated pesticidal agents which are more suitable for commercial manufacture.

It is a further object of the present invention to provide a wettable powder pesticidal composition containing a coated pesticidal agent.

SUMMARY OF THE INVENTION

The present invention describes coated pesticidal agents which retain a significant amount of their original activity after exposure to ultraviolet radiation.

The coated pesticidal agents of the present invention comprise a pesticidal agent core surrounded by a matrix which comprises about 2 to 25% by weight of a pH-dependent polymer, 0% to about 5% by weight of a plasticizer, about 5 to 45% by weight of an ultraviolet protector, 0% to about 75% by weight of a stilbene compound, 0% to about 10% by weight of a disintegrating agent, and 0% to about 10% by weight of a glidant.

The present invention further provides processes for the preparation of coated pesticidal agents, and wettable powder pesticidal compositions comprising the coated pesticidal agents.

BRIEF DESCRIPTION OF THE DRAWINGS

FIG. 1 depicts a schematic representation of the AcMNPV genome showing the location of the egt gene. In FIG. 1A the entire AcMNPV genome is presented in map units and as Eco RI and Hind III restriction maps. FIG. 1B depicts a more detailed map of the region located between map units 7.6 and 11.1 and shows the location of the egt gene.

FIG. 2A depicts a schematic representation of the egt gene region, which shows key restriction sites between map units 8.3 and 9.8 in the AcMNPV genome. FIG. 2B depicts the organization of open reading frames in the three forward (1, 2, 3) and three reverse (1', 2', 3') reading frames of the AcMNPV genome between map units 8.3 and 9.8. The large open reading frame in frame 2 marks the position of the protein coding region of the egt gene.

FIG. 3 depicts a schematic view of the organization and derivation of the DNA fragments used to assemble the (unloaded) AcMNPV V8 transfer vector NF4.

DETAILED DESCRIPTION OF THE INVENTION

Figure 3A:
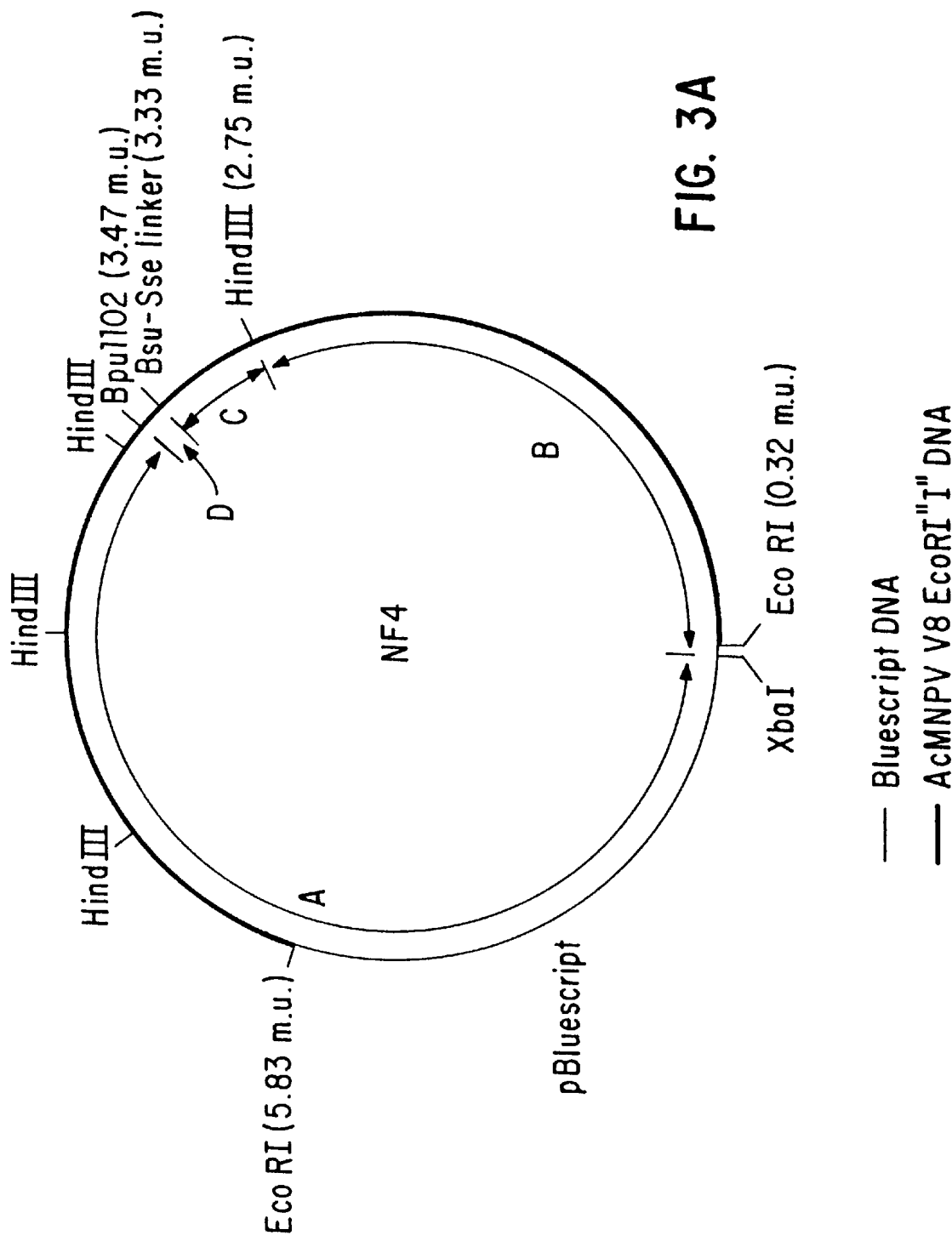
FIG. 3A depicts the manner in which fragments A–D are joined to form NF4.

The present invention provides processes for the preparation of coated pesticidal agents which avoid the problems associated with the methods known in the art.

One process of the present invention comprises:
a) blending a mixture of a pH-dependent polymer, a pesticidal agent, optionally a plasticizer, an ultraviolet protector, optionally a stilbene compound, optionally a disintegrating agent and optionally a glidant in an organic solvent such as acetone, $C_1$–$C_3$ alcohol, or combination thereof to produce a homogeneous suspension;
b) drying the homogeneous suspension of step (a); and optionally
c) milling the dried material of step (b).

Advantageously, the foregoing process of the present invention provides an efficient two or three step process for the preparation of coated pesticidal agents which avoids the use of multiple mixing and emulsifying steps, and avoids the use of numerous washing steps with flammable solvents. Further, the above process of this invention preferably utilizes an acetone/$C_1$–$C_3$alcohol solution which does not significantly inactivate pesticidal agents such as insecticidal pathogens. Other organic solvents taught in the art, such as methylene chloride, may significantly inactivate pesticidal agents such as insecticidal pathogens.

While the foregoing process is believed to be a significant advance over prior processes, a preferred process which avoids the use of the organic solvents has also been invented.

Uniquely, it has been found that coated pesticidal agents may be prepared by an aqueous process which comprises:
a) preparing an aqueous mixture of a pH-dependent polymer and optionally a plasticizer;
b) dissolving the pH-dependent polymer by adjusting the pH of the mixture of step (a) to about 8.5 to 10 with a base;
c) adding a pesticidal agent, an ultraviolet protector, optionally a stilbene compound, optionally a disintegrating agent and optionally a glidant to the solution of step (b), and blending to produce a homogeneous suspension;
d) drying the homogeneous suspension of step (c); and optionally
e) milling the dried material of step (d).

Advantageously, the aqueous process of this invention does not require the use of multiple mixing and emulsifying steps, and does not require the use of numerous washing steps with flammable solvents and further does not require the use of organic solvents.

The coated pesticidal agents of the present invention preferably have a particle size less than about 20 $\mu$m and more preferably have a particle size of about 2 $\mu$m to 10 $\mu$m. The homogeneous suspensions of this invention may be dried using any conventional drying technique. Preferably the suspensions are spray dried or air dried.

Preferred coated pesticidal agents prepared by the processes described hereinabove are those comprising a pesticidal agent core surrounded by a matrix which comprises about 2 to 25% by weight of a pH-dependent polymer, up to about 5% by weight of a plasticizer, about 5 to 45% by weight of an ultraviolet protector, up to about 75% by weight of a stilbene compound, up to about 10% by weight of a disintegrating agent, and up to about 10% by weight of a glidant.

The ratio of the pesticidal agent to the matrix is preferably about 1:1 to 1:10. And the ratio of acetone to the $C_1$–$C_3$alcohol is preferably about 1:9 to 9:1 and more preferably about 1:4 to 2:3. $C_1$–$C_3$alcohols suitable for use in the organic process include methanol, ethanol, isopropanol and n-propanol with isopropanol being preferred.

Pesticidal agents suitable for use in the present invention include chemical and biological insecticides, acaricides, nematicides and fungicides or mixtures thereof which are inactivated by ultraviolet radiation. Preferred pesticidal agents are insecticidal pathogens such as viral pathogens, bacterial pathogens and fungal pathogens. Viral pathogens suitable for use include wild gypsy moth NPV; *Autographa californica* NPV's such as AcMNPV E2, AcMNPV L1, AcMNPV V8, V8vEGTDEL and V8vEGTDEL-AaIT; Douglas fir tossock moth NPV; European pine saw fly NPV; and *Heliothis zea* NPV. Most preferred pesticidal agents for use in this invention are wild gypsy moth NPV, AcMNPV E2, AcMNPV L1, AcMNPV V8, V8vEGTDEL, V8vEGTDEL-AaIT, and *Heliothis zea* NPV.

AcMNPV E2 is described in copending U.S. patent application Ser. No. 08/009,264, filed on Jan. 25, 1993 which is incorporated herein by reference thereto. AcMNPV V8 and V8vEGTDEL are described in U.S. patent application Ser. No. (Attorney Docket 32,430), filed on Jul. 27, 1994 which is incorporated herein by reference thereto. V8vEGTDEL-AaIT is described in the examples hereinbelow.

pH-Dependent polymers suitable for use in the present invention include polymers which are essentially insoluble below about pH 5 such as methacrylic acid and methyl methacrylate copolymers, maleic anhydride and styrene copolymers and the like or mixtures thereof. Preferred pH-dependent polymers include methacrylic acid and methyl methacrylate copolymers, methacrylic acid and methyl methacrylate copolymer mixtures and maleic anhydride and styrene copolymers. Most preferred pH-dependent polymers are Eudragit®S (methacrylic acid and methyl methacrylate copolymer wherein the ratio of free carboxyl groups to esters is about 1:2; Röhm Pharma GmbH, Weiterstadt, Germany), Eudragit®L (methacrylic acid and methyl methacrylate copolymer wherein the ratio of free carboxyl groups to esters is about 1:1; Röhm Pharma GmbH) and mixtures thereof.

Plasticizers suitable for use in the present invention include any of the conventional agents known in the art such as polyethylene glycols, polypropylene glycols, diethyl phthalate, dibutyl phthalate, citric acid esters, castor oil, triacetin and the like or mixtures thereof with polyethylene glycols having a molecular weight of about 300 to 1,000 being preferred.

Ultraviolet protectors are used in the present invention to reduce the photoinactivation of the pesticidal agent. Ultraviolet protectors suitable for use include ultraviolet absorbers and ultraviolet reflectors or mixtures thereof. Ultraviolet absorbers include various forms of carbon such as carbon black; benzophenones such as 2-hydroxy-4-methoxybenzophenone (CYASORB®UV 9, Cytec Ind.), 2,2'-dihydroxy-4-methoxybenzophenone (CYASORB®UV 24, Cytec Ind.), 2-hydroxy-4-acryloyloxyethoxybenzophenone (CYASORB®UV 2098, Cytec Ind.), 2-hydroxy-4-n-octoxybenzophenone (CYASORB®UV 531, Cytec Ind.) and the like; and dyes such as congo red, malachite green, malachite green hydrochloride, methyl orange, methyl green, brilliant green, acridine yellow, FDC green, FDC yellow, FDC red and the like. Ultraviolet reflectors include titanium dioxide and the like. Preferred ultraviolet protectors include carbon black, benzophenones, dyes and titanium dioxide with carbon black, CYASORB®UV 9 and CYASORB®UV 24 being most preferred.

Bases suitable for use in the aqueous process of this invention include ammonium hydroxide, alkali metal hydroxides, alkaline earth metal hydroxides and the like with ammonium hydroxide being preferred. Certain insecticidal viral pathogens may be deactivated at a pH greater than 10. Therefore it is preferred to select an amount of a base which will adjust the pH to about 8.5 to 10 to ensure ready solubilization and lessen the chance of deactivation.

Stilbene compounds are used in this invention to enhance pesticidal activity of the pesticidal agent. Stilbene compounds suitable for use in this invention are described in U.S. Pat. No. 5,246,936 which is incorporated herein by reference thereto.

Preferred stilbene compounds are the analogues of 4,4'-diamino-2,2'-stilbene disulfonic acid, namely, a Calcofluor White (available from Sigma Chemical Co., St. Louis, Mo.) such as Calcofluor White M2R, Calcofluor White ABT, Calcofluor White LD, Calcofluor White RWP, etc.; a Blancophor (available from Mobay Chemicals, Pittsburgh, Pa.) such as Blancophor BBH, Blancophor MBBH, Blancophor BHC, etc.; an INTRAWITE® (a heterocyclic stilbene derivative, available from Crompton and Knowles Corp., Charlotte, N.C.) such as INTRAWITE®CF, etc.; a Leucophor (available from Sandoz Chemicals Corp., Charlotte, N.C.) such as Leucophor BS, Leucophor BSB, Leucophor EKB, Leucophor PAB, etc.; a Phorwhite (available from Mobay Chemicals, Pittsburgh, Pa.) such as Phorwite AR, Phorwite BBU, Phorwite BKL, Phorwite CL, Phorwite RKK, etc. and the like. Blancophor BBH, Calcofluor White M2R and Phorwite AR are the most preferred stilbene compounds.

Disintegrating agents are used in the present invention to shorten the milling time and enhance the particle size reduction of the dried material. Disintegrating agents suitable for use in this invention include salts of the condensation products of formaldehyde with the sulfonation products of polycyclic aromatic compounds, hydrophilic starches such as dextran, carboxy methylcellulose, polyvinyl pyrrolidine and the like or mixtures thereof. Preferred disintegrating agents are salts of the condensation products of formaldehyde with the sulfonation products of polycyclic aromatic compounds such as salts of the condensation products of formaldehyde with naphthalene sulfonates, petroleum sulfonates and lignin sulfonates with the sodium sulfonate of naphthalene formaldehyde condensates such as MORWET®D425 (Witco, Houston, Tex.), LOMAR®PW (Henkel, Cincinnati, Ohio) and DARVAN®1 (R.T. Vanderbilt Co., Norwalk, Conn.) being most preferred.

Glidants are used in the processes of this invention to keep the dried, coated pesticidal agents from sticking together. Glidants suitable for use in this invention include talc, magnesium stearate, calcium stearate, calcium sulfate and the like or mixtures thereof with talc being preferred.

Other additives such as preservatives, stabilizers (trehalose), anti-mold agents, anti-fungal agents, anti-bacterial agents and the like may also be included in the matrix of the present invention. Clearly, anti-fungal agents and anti-bacterial agents generally would not be used when fungal pathogens and bacterial pathogens, respectively, are coated.

Preferred coated pesticidal agents of the present invention are those comprising a pesticidal agent core surrounded by a matrix which comprises about 2 to 20% by weight of a pH-dependent polymer, up to about 3% by weight of a plasticizer, about 5 to 35% by weight of an ultraviolet protector, about 25 to 75% by weight of a stilbene compound, up to about 10% by weight of a disintegrating agent, and up to about 10% by weight of a glidant.

The present invention also provides a wettable powder pesticidal composition which comprises about 2 to 25% by weight of a wetting agent; about 2 to 40% by weight of a dispersing agent; about 10 to 70% by weight of a bulking agent; about 1 to 10% by weight of a flow enhancing agent; up to about 20% by weight of a pH-modifying agent; and about 5 to 75% by weight of a coated pesticidal agent which comprises a pesticidal agent core surrounded by a matrix which comprises about 2 to 25% by weight of a pH-dependent polymer, up to about 5% by weight of a plasticizer, about 5 to 45% by weight of an ultraviolet protector, up to about 75% by weight of a stilbene compound, up to about 10% by weight of a disintegrating agent, and up to about 10% by weight of a glidant.

Preferred wettable powder pesticidal compositions of the present invention are those comprising about 2 to 15% by weight of a wetting agent; about 2 to 15% by weight of a dispersing agent; about 10 to 60% by weight of a bulking agent; about 1 to 5% by weight of a flow enhancing agent; up to about 20% by weight of a pH-modifying agent; and about 5 to 75% by weight of a coated pesticidal agent which comprises a pesticidal agent core surrounded by a matrix which comprises about 2 to 25% by weight of a pH-dependent polymer, up to about 5% by weight of a plasticizer, about 5 to 45% by weight of an ultraviolet protector, up to about 75% by weight of a stilbene compound, up to about 10% by weight of a disintegrating agent, and up to about 10% by weight of a glidant.

Wetting agents suitable for use in the present invention include any of the conventional agents known in the art. Preferred wetting agents include anionic agents such as sodium N-methyl-N-oleoyltaurate, octylphenoxy polyethoxy ethanol, nonylphenoxy polyethoxy ethanol, sodium dioctyl sulfosuccinate, sodium dodecyl benzene sulfonate, sodium lauryl sulfate, sodium alkyl naphthalene sulfonate, sodium sulfonated alkyl carboxylate and the like or mixtures thereof. A mixture of sodium alkyl naphthalene sulfonate and sodium sulfonated alkyl carboxylate (MORWET®EFW, Witco) is the most preferred wetting agent.

Dispersing agents useful in the wettable powder pesticidal compositions of this invention include any of the conventional agents known in the art. Preferred dispersing agents are anionic agents such as salts of the condensation products of formaldehyde with the sulfonation products of polycyclic aromatic compounds, sodium lignosulfonate and the like or mixtures thereof with the sodium sulfonate of naphthalene formaldehyde condensates such as MORWET®D425 (Witco), LOMAR®PW (Henkel) and DARVAN ®1 (R.T. Vanderbilt Co.) being most preferred.

Bulking agents suitable for use in the compositions of the present invention include natural and synthetic clays and silicates, for example: natural silicas such as diatomaceous earths; magnesium silicates such as talcs; magnesium aluminum silicates such as attapulgites and vermiculites; aluminum silicates such as kaolinites, montmorillonites and micas; and hydrated aluminum silicates such as kaolin clay. Preferred bulking agents are hydrated aluminum silicates, aluminum silicates, magnesium silicates and magnesium aluminum silicates with kaolin clay being the most preferred bulking agent. Flow enhancing agents useful in the wettable powder pesticidal compositions of this invention are conventional flow enhancing agents known in the art with silicates such as calcium silicates being preferred.

pH-Modifying agents are used to maintain the pH of aqueous tank-mixes prepared from the compositions of this invention below about pH 5. pH-Modifying agents suitable for use include potassium hydrogen phthalate and organic acids with citric acid being preferred.

The wettable powder pesticidal compositions of the present invention may be prepared by blending a mixture of a wetting agent, a dispersing agent, a bulking agent, a flow enhancing agent and optionally a pH-modifying agent to form a premix. The premix is then blended with a coated pesticidal agent to form the desired wettable powder pesticidal composition of the present invention.

For the control of pests, the wettable powder pesticidal compositions of this invention are diluted with water to form an aqueous tank-mix and the tank-mix is applied directly to the pests, their breeding grounds, food supply or habitat.

Other ingredients such as attractants, stickers, antifoaming agents and the like may be added to the wettable powder compositions of this invention. However, those additional ingredients are generally added separately to the tank-mix. An adjuvant or mixture of adjuvants may also be added to the tank-mix.

In order to facilitate a further understanding of the invention, the following examples are presented primarily for the purpose of illustrating more specific details thereof. The invention should not be deemed limited thereby except as defined in the claims.

Unless otherwise noted, standard molecular biological techniques are utilized according to the protocols described in Sambrook et al. (1). Standard techniques for baculovirus growth and production are utilized according to the protocols described in Summers and Smith (2).

EXAMPLE 1

Preparation of Coated V8vEGTDEL Polyhedrin Inclusion Bodies—Aqueous Process

Ammonium hydroxide solution (28% $NH_3$) is added to a mixture of Eudragit®S100 (62 g, Röhm Pharma Co.) and PEG 400 (6.2 g, poly(ethylene glycol) average M.W. 400, Aldrich Chemical Co.) in deionized water (551.8 g) until a pH of about 9.4 is obtained. The resulting mixture is stirred for 30 minutes to obtain a solution. V8vEGTDEL polyhedrin inclusion bodies (62 g, average size about 2 µm, about $10^{11}$ bodies per gram), Blancophor BBH (248 g, stilbene brightner, Miles Inc.) and CYASORB®UV 9 (31 g, average particle size about 2 µm, Cytec Ind.) are added to the pH adjusted aqueous solution. The resultant mixture is stirred for 30 minutes and air dried with blending to obtain solid granules. The solid granules are air milled to give coated V8vEGTDEL polyhedrin inclusion bodies (362 g, average size about 5 µm). The coated V8vEGTDEL polyhedrin inclusion bodies prepared above are identified as composition 1 in Table II.

Using essentially the same procedure, but using the ingredients listed in Table I, the coated pesticidal agents identified as compositions 2–10 in Table II are prepared.

TABLE I

| Pesticidal Agent | |
|---|---|
| a. | V8vEGTDEL polyhedrin inclusion bodies |
| b. | *Heliothis zea* NPV |
| c. | AcMNPV |
| d. | 1:1 mixture of *Heliothis zea* NPV and AcMNPV |
| pH-Dependent Polymer | |
| e. | Eudragit ® S100 |
| Plasticizer | |
| f. | PEG 400 |
| UV-Protector | |
| g. | CYASORB ® UV 9 |
| h. | Charcoal |
| Stilbene Compound | |
| i. | Blancophor BBH |
| Glidant | |
| j. | Talc |

TABLE II

Coated Pesticidal Agent Compositions prepared by the Aqueous Process

Ingredient/wt/wt %

| Composition Number | Pesticidal Agent | pH-Dependent Polymer | Plasticizer | UV-Protector | Stilbene Compound | Glidant |
|---|---|---|---|---|---|---|
| 1 | a/15.15 | e/15.15 | f/1.52 | g/7.58 | i/60.61 | — |
| 2 | a/24.69 | e/12.35 | f/1.23 | g/12.35 | i/49.38 | — |
| 3 | a/21.74 | e/21.74 | f/2.17 | g/10.87 | i/43.48 | — |
| 4 | a/19.80 | e/9.90 | f/0.99 | g/9.90 | i/49.41 | — |
| 5 | a/17.86 | e/17.86 | f/1.79 | g/8.93 | i/53.57 | — |
| 6 | a/16.53 | e/8.26 | f/0.83 | g/8.26 | i/66.12 | — |
| 7 | b/4.81 | e/11.75 | f/1.18 | g/11.75 | i/70.51 | — |
| 8 | c/21.36 | e/9.71 | f/0.97 | g/9.71 | i/58.25 | — |
| 9 | d/8.41 | e/11.98 | f/1.20 | g/11.43 | i/66.98 | — |
| 10 | a/16.09 | e/3.17 | f/0.32 | h/32.17 | i/32.17 | j/8.04 |

EXAMPLE 2

Preparation of Coated V8vEGTDEL Polyhedrin Inclusion Bodies—Organic Process

V8vEGTDEL polyhedrin inclusion bodies (43.24 g, average size about 2 µm, about $10^{11}$ bodies per gram), Blancophor BBH (86.44 g) and CYASORB®UV 9 (31.93 g) are added to a solution of Eudragit®S100 (5.88 g) and PEG 400 (1.51 g) in a 30:70 acetone/isopropanol solution (195.15 g). The resultant mixture is stirred for several minutes and air dried with blending to obtain solid granules. The solid granules are milled through a 60 mesh screen to give coated V8vEGTDEL polyhedrin inclusion bodies having an average size of about 10 µm. The coated V8vEGTDEL polyhedrin inclusion bodies prepared above are identified as composition 11 in Table IV.

Using essentially the same procedure, but using the ingredients listed in Table III, the coated pesticidal agents identified as compositions 12–28 in Table IV are prepared.

TABLE III

Pesticidal Agent a. V8vEGTDEL polyhedrin inclusion bodies
b. Wild gypsy moth NPV pH-Dependent Polymer c. Eudragit ® S100
d. Cypress ® 48 (maleic anhydride/styrene copolymer, Cytec Ind.)

Plasticizer e. PEG 400

UV-Protector f. CYASORB ® UV 9
g. Charcoal
h. $TiO_2$

Stilbene Compound i. Blancophor BBH

Disintegrating Agent j. MORWET ® D425

Stabilizer k. Trehalose

EXAMPLE 3

Preparation of Wettable Powder Pesticidal Compositions

The coated V8vEGTDEL polyhedrin inclusion bodies identified as composition 1 in Table II (362 g) are added to a premix of MORWET®EFW (13.1 g), MORWET®D425 (26.2 g), kaolin clay (91.6 g), synthetic calcium sulfate (6.5 g, MICRO-CEL®E, Manville Co.) and citric acid (0.7 g). The resultant mixture is blended to obtain the wettable powder composition identified as composition 29 in Table V.

Using essentially the same procedure, the wettable powder compositions identified as compositions 30–53 in Table V are prepared.

TABLE IV

Coated Pesticidal Agent Compositions prepared by the Organic Process

Ingredient/wt/wt %

| Composition Number | Insecticidal Pathogen | pH-Dependent Polymer | Plasticizer | UV-Protector | Stilbene Compound | Disintegrating Agent | Stabilizer |
|---|---|---|---|---|---|---|---|
| 11 | a/23.76 | c/3.24 | e/0.83 | f/17.55 | i/47.50 | j/7.12 | — |
| 12 | a/70.18 | c/3.51 | e/1.75 | f/17.54 | — | j/7.02 | — |
| 13 | a/35.09 | c/3.86 | e/1.75 | f/17.54 | i/34.74 | j/7.02 | — |
| 14 | a/23.40 | c/4.91 | e/1.75 | f/17.52 | i/45.39 | j/7.02 | — |
| 15 | b/77.19 | c/3.51 | e/1.75 | f/17.54 | — | — | — |
| 16 | b/62.86 | c/5.71 | e/2.86 | f/28.57 | — | — | — |
| 17 | b/40.00 | c/3.64 | e/1.82 | f/18.18 | — | — | k/36.36 |
| 18 | b/77.19 | c/3.51 | e/1.75 | g/17.54 | — | — | — |
| 19 | b/62.86 | c/5.71 | e/2.86 | g/28.57 | — | — | — |
| 20 | b/77.19 | c/3.51 | e/1.75 | h/17.54 | — | — | — |
| 21 | b/62.86 | c/5.71 | e/2.86 | h/28.57 | — | — | — |
| 22 | b/26.83 | c/4.05 | e/2.02 | g/13.42 | — | — | k/53.67 |
| 23 | b/44.74 | c/2.24 | e/1.12 | f/11.22 | i/40.67 | — | — |
| 24 | b/23.16 | c/2.11 | e/1.05 | f/10.53 | i/63.16 | — | — |
| 25 | b/40.00 | c/3.64 | e/1.82 | g/18.18 | i/36.36 | — | — |
| 26 | b/20.37 | c/3.70 | e/1.85 | h/18.52 | i/55.56 | — | — |
| 27 | b/48.89 | c/4.44 | e/2.22 | f/22.22 | — | j/22.22 | — |
| 28 | b/23.66 | c/3.57 | e/1.79 | g/11.83 | — | j/11.83 | k/47.33 |

TABLE V

Wettable Powder Pesticidal Compositions

Ingredient/wt/wt %

| Composition Number | Coated Pesticidal Agent[1] | MORWET ® EFW | MORWET ® D425 | Kaolin Clay | MICRO-CEL ® E | Citric Acid | Sugar | MIRA-SPERSE ®[2] |
|---|---|---|---|---|---|---|---|---|
| 29 | 1/72.40 | 2.62 | 5.24 | 18.32 | 1.30 | 0.14 | — | — |
| 30 | 2/39.83 | 5.80 | 11.60 | 40.58 | 2.90 | 0.29 | — | — |
| 31 | 3/37.50 | 5.92 | 11.85 | 41.47 | 2.96 | 0.30 | — | — |
| 32 | 4/41.67 | 5.53 | 11.06 | 38.70 | 2.76 | 0.28 | — | — |
| 33 | 5/33.33 | 6.32 | 12.64 | 44.23 | 3.16 | 0.32 | — | — |
| 34 | 6/35.09 | 6.15 | 12.31 | 43.07 | 3.08 | 0.31 | — | — |
| 35 | 7/39.25 | 5.85 | 11.71 | 40.97 | 2.93 | 0.29 | — | — |
| 36 | 8/43.25 | 5.38 | 10.76 | 37.65 | 2.69 | 0.27 | — | — |
| 37 | 9/39.50 | 5.73 | 11.47 | 40.14 | 2.87 | 0.29 | — | — |
| 38 | 11/29.08 | 6.76 | 13.51 | 47.27 | 3.38 | — | — | — |
| 39 | 15/13.36 | 13.21 | 4.40 | 29.39 | 4.40 | — | 17.62 | 17.62 |
| 40 | 16/13.78 | 13.15 | 4.38 | 29.24 | 4.38 | — | 17.53 | 17.53 |
| 41 | 17/23.62 | 11.65 | 3.88 | 25.90 | 3.88 | — | 15.52 | 15.52 |
| 42 | 18/13.01 | 13.27 | 4.42 | 29.50 | 4.42 | — | 17.68 | 17.68 |
| 43 | 19/15.97 | 12.81 | 4.27 | 28.50 | 4.27 | — | 17.08 | 17.08 |
| 44 | 20/13.52 | 13.19 | 4.39 | 29.34 | 4.39 | — | 17.58 | 17.58 |
| 45 | 21/16.70 | 12.69 | 4.23 | 28.24 | 4.23 | — | 16.94 | 16.94 |
| 46 | 22/22.61 | 11.80 | 3.93 | 26.21 | 3.93 | — | 15.78 | 15.78 |
| 47 | 23/21.95 | 11.90 | 3.96 | 26.47 | 3.96 | — | 15.87 | 15.87 |
| 48 | 24/43.78 | 8.57 | 2.86 | 19.07 | 2.86 | — | 11.42 | 11.42 |
| 49 | 25/29.99 | 10.68 | 3.56 | 23.79 | 3.56 | — | 14.23 | 14.23 |
| 50 | 26/48.56 | 7.84 | 2.61 | 17.45 | 2.61 | — | 10.46 | 10.46 |
| 51 | 27/27.64 | 11.03 | 3.67 | 24.57 | 3.67 | — | 14.74 | 14.74 |
| 52 | 28/18.85 | 12.37 | 4.12 | 27.53 | 4.12 | — | 16.49 | 16.49 |
| 53 | 10/30.45 | 6.59 | 13.19 | 46.16 | 3.30 | 0.33 | — | — |

[1]The coated pesticidal agent is identified by the composition number from Table II or Table IV.
[2]MIRA-SPERSE ® is a 2-hydroxypropyl ether starch available from A. E. Staley Manufacturing Co., Decatur IL.

EXAMPLE 4

Insecticidal Evaluations of Non-irradiated and Irradiated Wettable Powder Pesticidal Compositions Against *L. dispar*

Wettable powder insecticidal pathogen compositions are suspended in distilled water and diluted to a concentration of $2.4 \times 10^5$ coated insecticidal polyhedrin inclusion bodies per mL. The resultant suspension (0.5 mL) is pipetted to the surface of wheat germ diet in a 180 mL plastic cup. Each cup is exposed to ultraviolet radiation (one Westinghouse BLB bulb and one Phillips F40 UVB bulb set three inches apart, the distance from the center line of the radiation source and the diet surface is 4 inches) for either 0 or 80 minutes. Ten second instar *L. dispar* caterpillars are placed in each cup. The cups are covered and maintained in darkness at 29° C., 55–60% relative humidity. After 13 days, the cups are examined and mortality by virus infection is determined.

The results are summarized in Table VI wherein the effectiveness of each composition is expressed as the percent of original activity remaining after ultraviolet exposure (% OAR), i.e. % mortality caused by irradiated composition÷% mortality caused by non-irradiated composition×100. The control composition used in the evaluations is identified below.

Control Composition

| Ingredient | wt/wt % |
|---|---|
| [1]Coated insecticidal pathogen | 11.19 |
| MORWET ® EFW | 13.54 |
| MORWET ® D425 | 4.51 |
| Kaolin Clay | 30.12 |
| MICRO-CEL ® E | 4.51 |
| Sugar | 18.06 |
| MIRA-SPERSE ® | 18.06 |

[1]93.62 wt/wt % wild gypsy moth NPV, 4.26% wt/wt % Eudragit ® S100 and 2.13 wt/wt % PEG 400.

TABLE VI

Insecticidal Evaluations Against *L. dispar*

| Composition Number[1] | % Mortality Irradiated | % Mortality Non-Irradiated | % OAR[2] |
|---|---|---|---|
| Control | 47.5 | 100.0 | 47.5 |
| 39 | 70.0 | 100.0 | 70.0 |
| 40 | 76.7 | 99.2 | 77.2 |
| 41 | 87.5 | 99.2 | 88.2 |
| 42 | 91.7 | 98.3 | 93.2 |
| 43 | 98.3 | 99.2 | 99.2 |
| 44 | 57.5 | 100.0 | 57.5 |
| 45 | 65.0 | 96.7 | 67.3 |
| 46 | 82.5 | 98.3 | 84.0 |
| 47 | 91.7 | 98.3 | 93.2 |
| 48 | 90.0 | 99.2 | 90.8 |
| 49 | 90.0 | 98.3 | 91.6 |
| 50 | 87.9 | 100.0 | 87.9 |

TABLE VI-continued

Insecticidal Evaluations Against *L. dispar*

| Composition Number[1] | Irradiated | Non-Irradiated | % OAR[2] |
|---|---|---|---|
| | % Mortality | | |
| 51 | 77.5 | 99.2 | 78.2 |
| 52 | 90.0 | 99.2 | 90.7 |

[1]Composition number from Table V.
[2]Percentage of original activity remaining after ultraviolet exposure.

EXAMPLE 5

Insecticidal Evaluations of Wettable Powder Pesticidal Compositions Against *Helicoverpa zea*

Plastic bioassay trays containing 32 open-faced wells (4×4×2.5 cm, L×W×H, C-D International, Inc.) per tray are utilized as test arenas in this evaluation. Five mL of Stoneville diet (soybean/wheat germ) is poured into each tray-well and allowed to harden. Aqueous suspensions (0.4 mL) of wettable powder insecticidal pathogen compositions are evenly spread over the surface of the hardened diet to provide from $4 \times 10^5$ to $4 \times 10^7$ V8vEGTDEL coated or uncoated polyhedrin inclusion bodies per well. After drying the trays in a laminar flow hood, one three-day-old *Helicoverpa zea* larvae is placed on the surface of the diet in each tray-well. The wells are covered with an adhesive, vented clear plastic sheet (C-D International, Inc.), held under constant fluorescent light and at a temperature of about 27° C. Five days and ten days after treatment, the wells are examined and larval mortality measurements are made.

The results are summarized in Table VII. The control compositions used in the evaluations are identified below.

| Control Composition | Ingredient | wt/wt % |
|---|---|---|
| A | Uncoated V8vEGTDEL polyhedrin inclusion bodies | 10.00 |
| | MORWET ® EFW | 8.53 |
| | MORWET ® D425 | 17.06 |
| | Kaolin Clay | 59.71 |
| | MICRO-CEL ® E | 4.27 |
| | Citric Acid | 0.43 |
| B | Uncoated V8vEGTDEL polyhedrin inclusion bodies | 8.69 |
| | MORWET ® EFW | 8.71 |
| | MORWET ® D425 | 17.40 |
| | Kaolin Clay | 60.86 |
| | MICRO-CEL ® E | 4.35 |

TABLE VII

Insecticidal Evaluations Against *Helicoverpa zea*

| Composition Number[1] | Concentration (bodies/well) | % Mortality 5 Days | % Mortality 10 Days |
|---|---|---|---|
| Control A | $4 \times 10^7$ | 49 | 91 |
| | $4 \times 10^6$ | 47 | 93 |
| | $4 \times 10^5$ | 29 | 63 |
| Control B | $4 \times 10^7$ | 33 | 75 |
| | $4 \times 10^6$ | 35 | 70 |
| | $4 \times 10^5$ | 18 | 47 |
| 29 | $4 \times 10^7$ | 77 | 100 |
| | $4 \times 10^6$ | 58 | 100 |
| | $4 \times 10^5$ | 35 | 77 |
| 38 | $4 \times 10^7$ | 43 | 95 |
| | $4 \times 10^6$ | 45 | 80 |
| | $4 \times 10^5$ | 25 | 56 |

[1]Composition number from Table V.

EXAMPLE 6

Evaluation of Non-irradiated and Irradiated Wettable Powder Compositions against *H. zea* and *H. virescens*

Plastic bioassay trays containing 32 open-faced wells (4×4×2.5 cm, L×W×H, C-D International, Inc.) per tray are utilized as test arenas in this evaluation. Five mL of Stoneville diet (soybean/wheat germ) is poured into each tray-well and allowed to harden. Aqueous suspensions (0.4 mL) of the wettable powder insecticidal pathogen compositions are evenly spread over the surface of the hardened diet to provide $4 \times 10^6$ V8vEGTDEL coated or uncoated polyhedrin inclusion bodies per well. Some of the treated trays are then held under ultraviolet lamps (two FS4OUVB bulbs set 30 cm above the trays, Phillips Co.) for either one or two hours. Trays selected for two hours of irradiation are provided with an additional 0.4 mL of deionized water per well at the one hour time interval to prevent the diet from overdrying and cracking. All trays are then infested with a single three-day-old *H. zea* or four-day-old *H. virescens* larvae. The wells are covered with an adhesive, vented clear plastic sheet (C-D International, Inc.), held under constant fluorescent light and at a temperature of about 27° C. Ten days after treatment, the wells are examined and larval mortality measurements are made.

The results are summarized in Table VIII. The control composition used in the evaluations is identified below.

| Control Composition | | |
|---|---|---|
| Ingredient | | wt/wt % |
| Uncoated V8vEGTDEL polyhedrin inclusion bodies | | 4.93 |
| MORWET ® EFW | | 9.01 |
| MORWET ® D425 | | 18.02 |
| Kaolin Clay | | 63.09 |
| MICRO-CEL ® E | | 4.51 |
| Citric Acid | | 0.45 |

TABLE VIII

Evaluation of non-irradiated and irradiated wettable
powder compositions against H. zea and H. virescens

| Composition Number | Irradiation Exposure (hours) | Mean % Larval Mortality | |
|---|---|---|---|
| | | H. zea | H. virescens |
| Control | 0 | 59 | 77 |
| | 1 | 46 | 56 |
| | 2 | 40 | 36 |
| 53[1] | 0 | 91 | 89 |
| | 1 | 90 | 87 |
| | 2 | 83 | 56 |

[1]Composition number from Table V.

EXAMPLE 7

Solvent Compatibility Evaluations

The following evaluation is used to determine the effect of various solvents and mixtures thereof on the activity of *Autographa californica* polyhedrin inclusion bodies. A mixture of *Autographa californica* polyhedrin inclusion bodies (0.55 g) and the appropriate solvent or solvent mixture (1.5 mL) is held in a conical tube for 10 or 60 minutes. The tubes are then centrifuged and the supernatant is decanted. The solids are dried under vacuum in a dessicator. The dried solids are then evaluated against *Heliothis virescens* according to the procedure described in Example 6 (no irradiation).

The results are summarized in Table IX. As can be seen from the data in Table IX, the *Autographa californica* polyhedrin inclusion bodies mixed with methylene chloride for 10 and 60 minutes are significantly less active against *Heliothis virescens* than the bodies mixed with acetone, isopropanol and a 30:70 acetone/isopropanol mixture.

TABLE IX

| Solvent Compatibility Evaluations | | | |
|---|---|---|---|
| Solvent | Time held (minutes) | Rate (bodies/well) | % Mortality |
| Acetone | 10 | $4 \times 10^2$ | 19 |
| | 60 | $4 \times 10^2$ | 25 |
| | 10 | $4 \times 10^4$ | 100 |
| | 60 | $4 \times 10^4$ | 100 |
| Isopropanol | 10 | $4 \times 10^2$ | 31 |
| | 60 | $4 \times 10^2$ | 13 |
| | 10 | $4 \times 10^4$ | 100 |
| | 60 | $4 \times 10^4$ | 100 |
| Acetone/Isppropanol (30:70) | 10 | $4 \times 10^2$ | 34 |
| | 60 | $4 \times 10^2$ | 19 |
| | 10 | $4 \times 10^4$ | 100 |
| | 60 | $4 \times 10^4$ | 100 |
| Methylene chloride | 10 | $4 \times 10^2$ | 9 |
| | 60 | $4 \times 10^2$ | 6 |
| | 10 | $4 \times 10^4$ | 84 |
| | 60 | $4 \times 10^4$ | 19 |

EXAMPLE 8

Construction of Strain V8vEGTDEL

To construct a recombinant AcMNPV (strain V8; ATCC VR-2465) virus incapable of expressing a functional egt gene, a DNA fragment containing the AcMNPV egt gene and extending from the Pst I site at m.u. 7.6 to the Bam HI site at m.u. 11.1 of the AcMNPV genome is first inserted into pUC19 (Sigma Chemical Co., St. Louis, Mo.) between the Pst I and Eco RI sites of the pUC19 polylinker (see FIG. 1 for a schematic restriction map of the AcMNPV genome and the placement of sites with respect to the egt gene). The Bam HI end of the AcMNPV DNA fragment and the Eco RI end of the pUC19 polylinker are both filled in by treatment with T4 DNA polymerase prior to fragment ligation so as to facilitate the fragment joining in such a way that the Eco RI site in the polylinker region of the product is destroyed. The resulting plasmid is designated pUCBCPsB.

Plasmid pUCBCPsB is cleaved with restriction endonuclease Xba I (see FIG. 2 for the placement of these sites within the egt gene) and treated with T4 DNA polymerase to fill in the overhanging end at the Xba I cleavage site. The linearized plasmid is then cleaved with Eco RI and the small Xba I/Eco RI fragment is discarded. The *Escherichia coli* lacZ gene, excised from pSKS104 (3) with Eco RI and Aha III, is then inserted between the Eco RI and filled in Xba I sites. The resultant plasmid is designated pEGTZ. In this plasmid, the inserted lacZ gene is in frame with the preceding egt coding sequences. Alternatively, the plasmid pEGTDEL is constructed by simply ligating the Eco RI and Xba I sites together (after both sites have been blunt-ended) without inserting any sequences between them.

Plasmid pEGTZ is then cotransfected with AcMNPV V8 DNA into SF cells as described in Summers and Smith (2). This procedure allows for homologous recombination to take place between sequences in the viral and plasmid DNAs, resulting in replacement of the viral egt gene with the egt-lacZ gene fusion from pEGTZ. Because the remaining egt coding sequence is in frame with the lacZ sequences, the resulting virus (designated V8vEGTZ) produces a fusion protein whose expression gives rise to blue viral plaques in the presence of a chromogenic indicator such as 5-bromo-4-chloro-3-indolyl-β-D-galactopyranoside (X-gal).

Recombinant virus V8vEGTDEL is obtained by cotransfecting the plasmid pEGTDEL and DNA from the virus V8vEGTZ into SF cells. Homologous recombination results in the replacement of the egt-lacZ fusion gene in V8vEGTZ with the deleted egt gene from pEGTDEL. The recombinant virus V8vEGTDEL is identified by its failure to form blue plaques in the presence of X-gal.

EXAMPLE 9

Construction of T-NF002, an $occ^-$/β-$gal^+$ Derivative of V8vEGTDEL

As a prelude to the construction of recombinant derivatives of V8vEGTDEL-AaIT an intermediate virus vector is constructed in which the polyhedrin gene is partially deleted and replaced by the *Escherichia coli* lacZ gene. The resulting virus is unable to form viral occlusions (occlusion-negative; $occ^-$) and gives rise to blue viral plaques in the presence of a chromogenic indicator X-gal (β-$gal^+$). T-NF002 is constructed by cotransfecting SF cells with V8vEGTDEL DNA and the transfer vector pVL941-500Bgal, in which part of the AcMNPV polyhedrin gene has been replaced by the *Escherichia coli* lacZ gene (4). T-NF002 is identified as a blue plaque which is devoid of viral occlusions when the transfection supernatants are plated on SF cells in the presence of the chromogenic indicator X-gal.

EXAMPLE 10

Construction of the Unloaded AcMNPV V8 Transfer Vector NF4

Transfer vector NF4 is designed to facilitate the insertion of foreign genes into the AcMNPV V8 genome by homologous DNA recombination at a site 92 bp upstream of the polyhedrin gene. To construct NF4 an 8 bp Bgl II linker (5'-CAGATCTG-3'; Boehringer-Mannheim, Indianapolis, Ind.) is first inserted into the unique Eco RV site in the polylinker of pBluescript® II KS-(Stratagene, La Jolla, Calif.), so that the Eco RV site is destroyed. This plasmid is designated AC0039.1. An Eco RI fragment extending from 0.32 m.u. to 5.83 m.u. in the AcMNPV V8 genome (Eco RI fragment "I" in FIG. 1) is then cloned into the unique Eco RI site of AC0039.1 to yield intermediate plasmid NF3.

NF4 is derived from NF3 by the net insertion of a 22 bp double stranded DNA sequence ("Bsu-Sse linker") into NF3 at a point located 92 bp upstream of the AcMNPV V8 polyhedrin gene. The inserted sequence contains recognition sites for restriction endonucleases Bsu36I and Sse8387I, as shown below:

```
     Bsu36I      Sse8387I
5' - CCTCAGGGCAGCTGCCTGCAGG - 3'
3' - GGAGTCCCGTCGACGGACGTCC - 5'  (SEQ ID NO:1)
```

Because AcMNPV V8 does not contain a convenient restriction site at the desired point of Bsu-Sse linker insertion, NF4 is assembled by simultaneous ligation of four DNA fragments, denoted A–D in FIG. 3A. All fragments are purified by agarose gel electrophoresis.

Figure 3B:
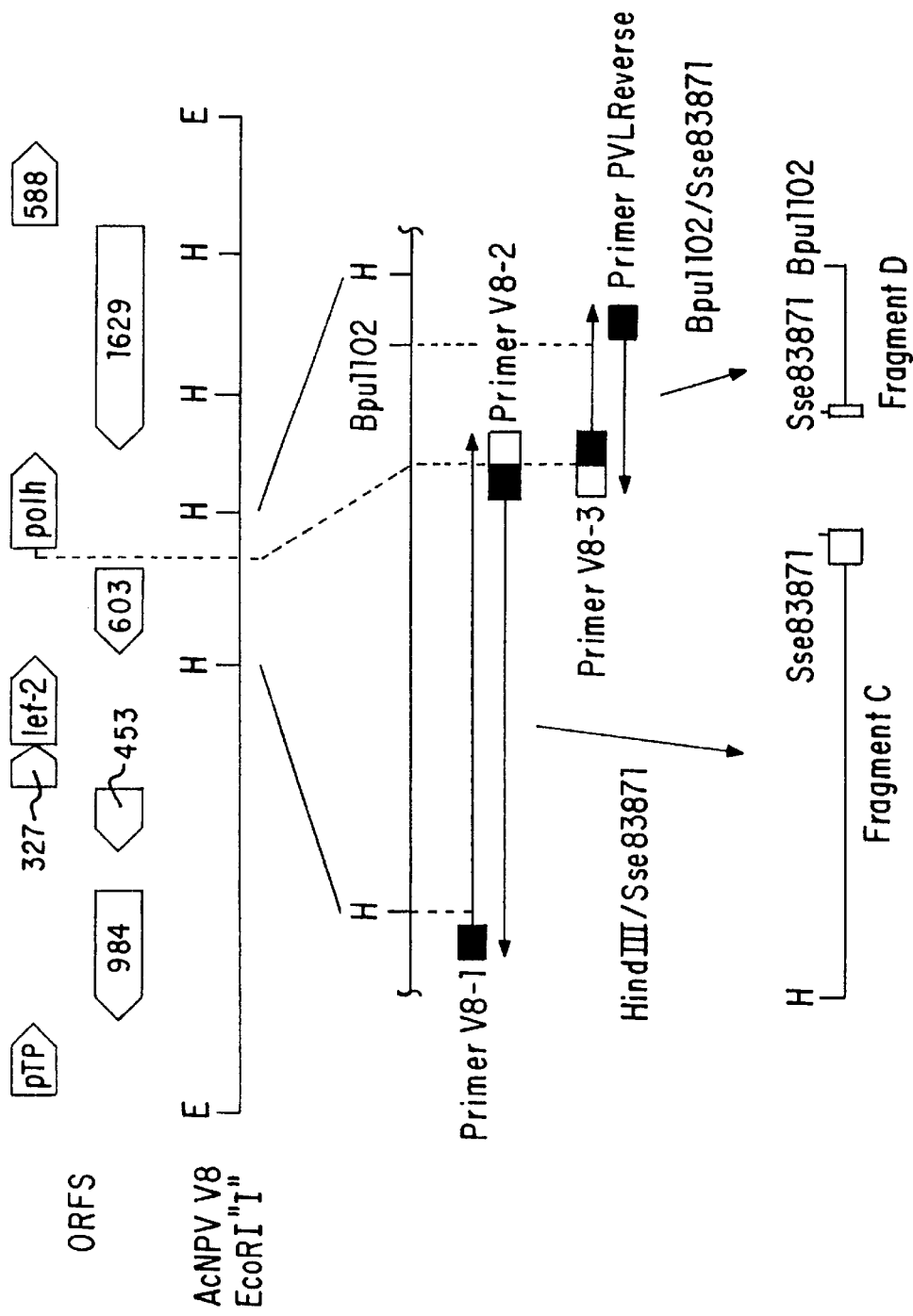
FIG. 3B depicts a schematic representation of the process used for the preparation of Fragments C and D. The arrows above the linear restriction map of the AcMNPV V8 Eco RI "I" fragment depict the location and transcriptional polarity of the major open reading frames (ORFS) located between map units 0.32 and 5.83 in the AcMNPV genome. The symbols "H" and "E" depict the positions of the recognition sites for restriction endonucleases Hind III and Eco RI, respectively.

Fragment A is prepared by digesting NF3 with restriction endonuclease Bpu1102 I, dephosphorylating the termini with calf intestine alkaline phosphatase, cleaving the DNA with Xba I and isolating the large (6.1 kb) Xba I/Bpu1102 I fragment. Fragment B is prepared by digesting NF3 with Hind III, dephosphorylating the termini with calf intestine alkaline phosphatase, cleaving the DNA with Xba I and isolating the 3.26 kb Hind III/Xba I fragment. Fragments C and D are prepared as shown in FIG. 3B from DNA fragments synthesized by PCR amplification using the AcMNPV V8 EcoRI "I" fragment in NF3 as the DNA template.

The primers for the synthesis of fragment C are:

```
V8-1: 5'-GCTCTGACGCATTTCTACAACCACGACTCC-3'  (SEQ ID NO:2)

Sse8387I       Bsu36I
V8-2: 5'-TAATcctgcaggcagctgccctgaggATCAGCAACTATATATTAAGCCG-3'  (SEQ ID NO:3)
```

Primer V8-1 is the forward primer in the PCR reaction and hybridizes with the complementary DNA strand of AcMNPV V8 genome at m.u. 2.65. Primer V8-2 is composed of two parts. Residues 1 through 4 and 27 through 49 (shown capitalized above) are colinear with the complementary AcMNPV V8 DNA sequence located 89 to 92 bp and 93 to 115 bp, respectively, upstream of polyhedrin gene translational start site. This segment of the primer is represented by the solid box portion of primer V8-2 in FIG. 3B. Residues 5 through 26 of primer V8-2 (shown in lower case above) comprise the complementary strand of the Bsu-Sse linker sequence being inserted 92 bp upstream of the polyhedrin gene translational start site in the AcMNPV V8 genome. This segment of the primer is not complementary to any natural AcMNPV DNA sequences and is represented by the open box portion of primer V8-2 in FIG. 3B. Following PCR synthesis, the fragment is digested with Hind III and Sse8387 I to yield fragment C, which is purified by gel electrophoresis.

The primers for the synthesis of fragment D are:

```
               Sse8387I
V8-3: 5' - gctgcctgcaggATTATGTAAATAATTAAAATGATAACCATCTCGC - 3'  (SEQ ID NO:4)

PVLReverse: 5' - GGATTTCCTTGAAGAGAGTGAG - 3'  (SEQ ID NO:5)
```

Primer V8-3 is composed of two parts. Residues 1 through 12 (shown in lower case above) comprise the 3' half of the top strand of the Bsu-Sse linker and are not complementary to any natural AcMNPV DNA sequences. This segment of the primer contains only the Sse8387I recognition site and is represented by the open box portion of primer V8-3 in FIG. 3B. Residues 13 through 46 are colinear with the AcMNPV V8 DNA sequence located 92 to 59 bp upstream of polyhedrin gene translational start site. This segment of the primer is represented by the solid box portion of primer V8-3 in FIG. 3B. Primer PVLReverse hybridizes to the complementary strand of the AcMNPV V8 genome at a point located 205 to 226 bp downstream of the polyhedrin gene translational start site. Following PCR synthesis, the fragment is digested with Bpu1102 I and Sse8387 I to yield fragment D, which is purified by gel electrophoresis.

NF4 is assembled by incubating equimolar amounts of fragments A–D (25 fmol each) for 16 h at 15° C. in a 10 μl ligation reaction containing 20 mM Tris-HCl (pH 7.5)-10 mM $MgCl_2$-10 mM DTT-0.5 mM ATP and 200 units T4 DNA ligase (New England Biolabs, Beverly, Mass.). After transformation of E. coli with the contents of the ligation reaction, plasmids having the structure of NF4 are identified by restriction enzyme analysis.

EXAMPLE 11

Construction of a Gene Cassette Containing the Manduca sexta Adipokinetic Hormone Gene Signal Sequence Plus the Codon Optimized cDNA Sequence Encoding AaIT Recombinant viral insecticides are viruses, especially baculoviruses, whose insecticidal properties have been enhanced by the addition of one or more foreign genes that encode insect-specific toxins (5–7), peptide hormones (8) or enzymes (9). The peptide AaIT, which is found in the venom of the North African scorpion Androctonus australis, is an example of such an insect-specific toxin (6). When AaIT is injected into the body cavity of an insect larva, it binds selectively to voltage-sensitive sodium channels and causes a contractile paralysis. Chronic administration of the toxin, which can be achieved by infecting insect larvae with AaIT-producing viruses, is associated with a prolonged state of paralysis and eventual death.

Figure 4:
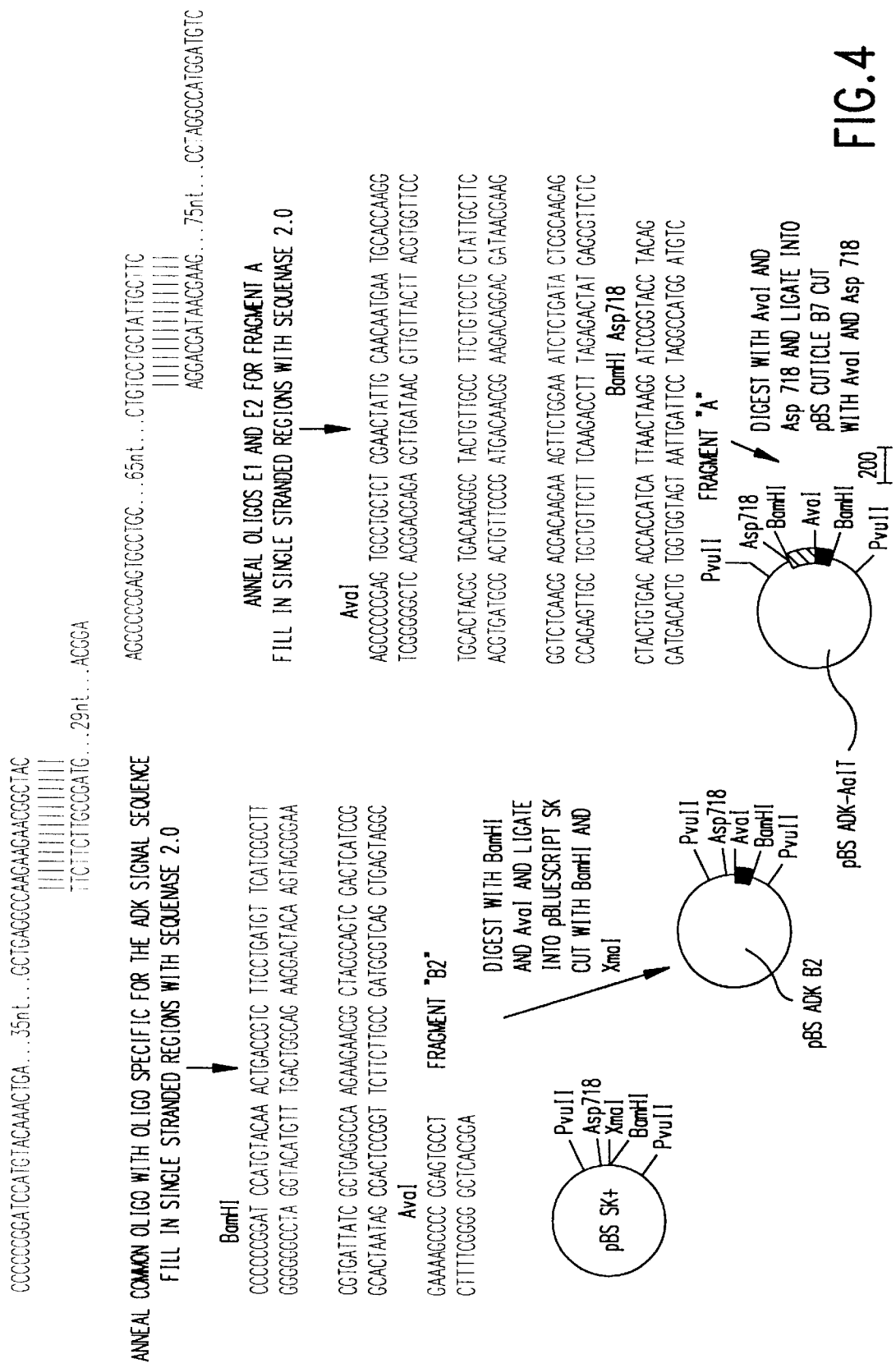
FIG. 4 depicts details of the construction of the plasmid pBS ADK-AaIT, which contains the heterologous adipokinetic hormone gene signal sequence and a codon optimized cDNA sequence encoding AaIT.

A gene cassette encoding the mature AaIT toxin linked to an insect signal peptide from the Manduca sexta adipokinetic hormone (ADK) gene is synthesized and assembled in two pieces: A "B2" fragment consisting of DNA coding for the ADK signal sequence plus the amino terminal portion of the toxin coding region, and an "A" fragment, which encodes the remainder of the toxin coding region. Each of fragments A and B2 is made by annealing a pair of oligomers containing a 15 bp overlap purchased from New England Biolabs (Beverly, Mass.). Sequenase™ 2.0, a DNA polymerase (United States Biochemical Corporation, Cleveland, Ohio), is used to complete the double stranded molecule, which contains the ADK signal sequence plus the codon optimized cDNA sequence encoding AaIT. The following is a list of the oligomers used in the construction of this construct:

regions. This results in a double stranded molecule which contains an Ava I site at the 5' terminus and nested Bam HI and Asp 718 sites following the 3' end of the toxin coding region. The Bam HI and Asp 718 sites are introduced in order to facilitate cloning. Fragment A is then digested with Ava I and Asp 718. The fragment B2-containing plasmid, pBS ADK B2, is also digested with Ava I and Asp 718 and Fragment A is subcloned into the digested plasmid. In FIG. 4, the resulting plasmid is designated pBS ADK-AaIT. After the ligation of fragment A into pBS ADK B2, the ligated DNA is used to transform competent DH5α E. coli. Minipreps of plasmid DNA are prepared from the resulting bacterial colonies. Restriction enzyme analysis is used to determine which colonies contain the desired recombinant DNA. Further restriction enzyme analysis, followed by DNA sequencing, is used to confirm the integrity of plasmid pBS ADK-B2.

Fragment A

E1      5' AGCCCCCGAG TGCCTGCTCT CGAACTATTG

CAACAATGAA TGCACCAAGG TGCACTACGC

TGACAAGGGC TACTGTTGCC TTCTGTCCTG

CTATTGCTTC 3' (SEQ ID NO:6)

E2      5' CTGTAGGTAC CGGATCCTTA GTTAATGATG

GTGGTGTCAC AGTAGCTCTT GCAGTATCA

GAGATTTCCA GAACTTTCTT GTCGTCGTTG

AGACCGAAGC AATAGCAGGA 3' (SEQ ID NO:7)

Fragment B2

Common  5' AGGCACTCGG GGGCTTTTCC GGATGAGGTC

GACTGCGTAG CCGTTCTTCT T 3' (SEQ ID NO:8)

ADK     5' CCCCCCGGAT CCATGTACAA ACTGACCGTC

TTCCTGATGT TCATCGCCTT CGTGATTATC

GCTGAGGCCA AGAAGAACGG CTAC 3' (SEQ ID NO:9)

FIG. 4 depicts the construction strategy for the gene cassette which contains the AaIT gene linked to the Manduca sexta ADK signal sequence. In the first step, oligonucleotides 'Common' and 'ADK' are annealed and the single stranded regions are filled in using Sequenase™ 2.0. The filled in fragment consists of a 12 nucleotide upstream noncoding region containing the BamHI site required for cloning, the coding region for the ADK signal sequence, and the first 15 nucleotides encoding the first five aminoterminal amino acids of AaIT. This short piece of double-stranded DNA is digested with Bam HI and Ava I and subcloned into pBluescript SK+ (Stratagene, LaJolla, Calif.) which has been digested with Xma I and Bam HI. Positive subclones are verified by the presence of a Pvu II fragment larger than the 445 bp fragment present in pBluescript SK+ alone. There is a single base pair mismatch between the overhangs for the Ava I and Xma I sites. Clones which have corrected this mismatch are selected by the appropriate restriction enzyme digestions. In FIG. 4, the resulting plasmid is designated pBS ADK B2.

To construct the A fragment encoding the bulk of the AaIT coding region, oligonucleotides 'E1' and 'E2' are annealed and Sequenase™ 2.0 is used to fill in the single stranded

EXAMPLE 12

Insertion of the ADK-AaIT gene cassette into occ⁻ Baculovirus Transfer Vectors

The ADK-AaIT gene cassette of Example 11 is isolated as a Bam HI fragment from pBS ADK-AaIT and subcloned into the pVL985 baculovirus transfer vector DNA (4) which had been digested with Bam HI and treated with calf intestine alkaline phosphatase. The resulting plasmid is designated pVL985/ADK-AaIT. Restriction enzyme analysis followed by sequencing of the insert is used to confirm the correct orientation and integrity of pVL985/ADK-AaIT.

Samples of an E. coli strain HB101 harboring the transfer vector AC0055.1 have been deposited previously by applicants' assignee with the American Type Culture Collection, 12301 Parklawn Drive, Rockville, Md. 20852, U.S.A. and have been assigned ATCC accession number 69166. AC0055.1 contains a gene cassette in which the AaIT gene sequence of Example 11 is linked to a Drosophila cuticle gene signal sequence rather than the Manduca sexta adipokinetic hormone gene signal sequence. Using this deposited material, one of ordinary skill in the art can substitute the adipokinetic hormone gene signal sequence described above for the cuticle gene signal sequence which has the following DNA sequence:

```
Cuticle   5' CCCCCCGGAT CCATGTTCAA GTTCGTGATG
             ATCTGCGCCG TCCTCGGCCT GGCTGTGGCC
             AAGAAGAACG GCTAC 3' (SEQ ID NO:10)
```

EXAMPLE 13

Figure 5:
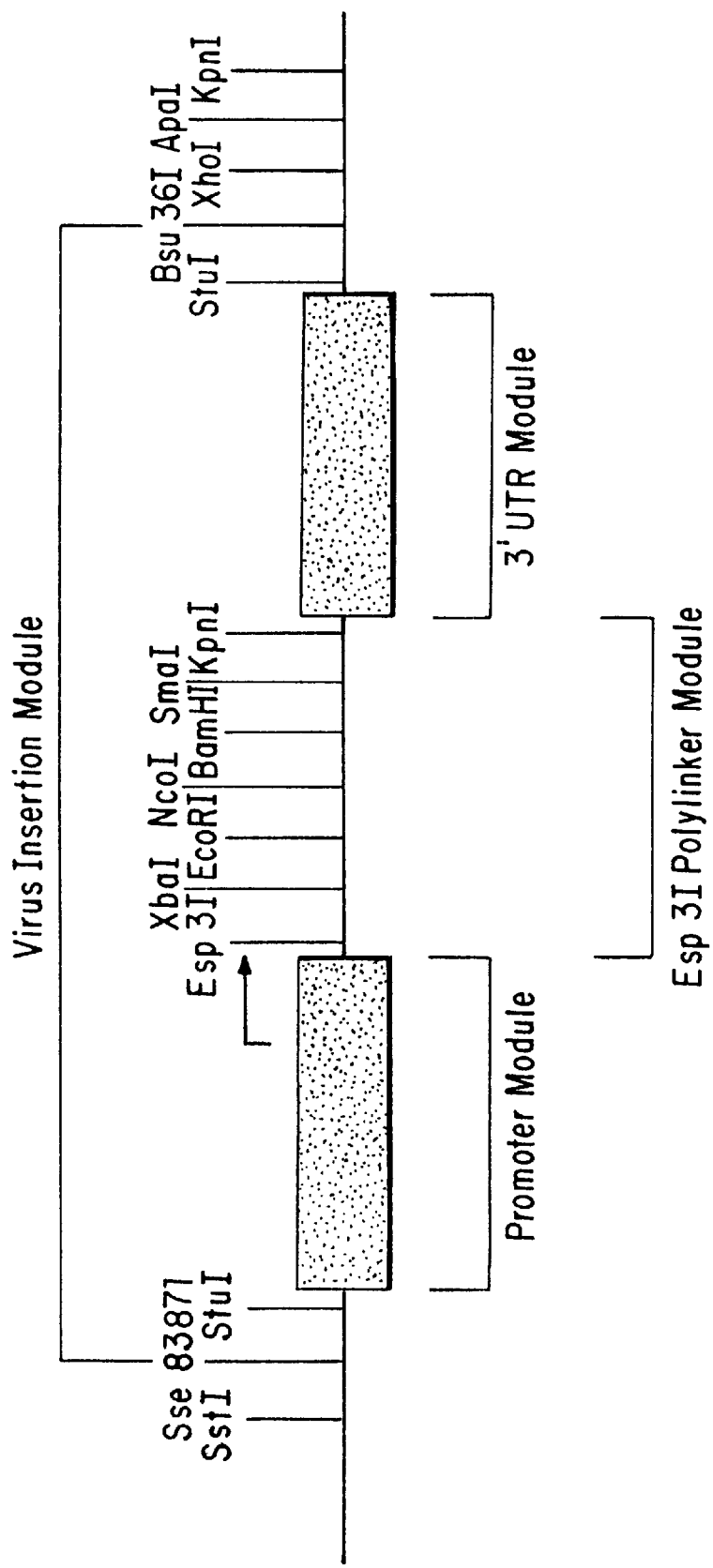
FIG. 5 depicts a portion of a modular expression vector with Bsu 36I and Sse 8387I sites at opposite ends of an expression cassette containing a promoter module, a polylinker module and a 3' UTR module. The polylinker module contains an Esp 3I recognition site. The region bounded by the outermost Bsu 36I and Sse 8387I sites is defined as the virus insertion module.

Insertion of the ADK-AaIT gene cassette into Baculovirus Modular Expression Vectors Since the ADK-AaIT gene cassette in the pVL985/ADK-AaIT transfer vector of Example 13 replaces part of the viral polyhedrin gene, the usefulness of this transfer vector is limited to the construction of occlusion-negative (occ$^-$) recombinant viruses that express AaIT. It is also advantageous to insert the ADK-AaIT into the AcMNPV genome at a site which allows the recombinant virus to form viral occlusion bodies. One site which is useful for this purpose is the site of Bsu-Sse linker in the (unloaded) AcMNPV V8 transfer vector NF4 of Example 10. This site is located between the viral polyhedrin and ORF 603 open reading frames and does not disrupt any known viral functions (cf. FIG. 3). However, since the ADK-AaIT gene cassette of Example 12 does not contain the regulatory sequences necessary for the transcription and 3' processing (polyadenylation) of ADK-AaIT mRNA, it is first necessary to insert the ADK-AaIT gene cassette into an expression vector which supplies these critical regulatory elements. One such vector is pMEV1.1, which is an Esp 3I-based Modular Expression Vector based on the general design shown in FIG. 5. pMEV1.1 is constructed in pBluescript KS- and is comprised of the following components: (1) a virus insertion module, which is delineated by recognition sites for restriction enzymes Sse 8387I and Bsu 36I; (2) a promoter module, which in the case of pMEV1.1 consists of the promoter and 5' untranslated region of the AcMNPV DA26 gene (10); (3) a polylinker module, which is used to facilitate insertion of the gene cassette whose expression is desired; and (4) a 3' UTR (untranslated region) which supplies a site for the 3' processing and polyadenylation of mRNA. The 3' UTR in pMEV1.1 consists of the 3' UTR of the AcMNPV basic protein (6.9K) gene (11). Samples of an E. coli strain DH5α harboring pMEV1.1 (AC0064.1) have been deposited by applicants' assignee with the American Type Culture Collection, 12301 Parklawn Drive, Rockville, Md. 20852, U.S.A., on Apr. 7, 1993, and have been assigned ATCC accession number 69275.

Figure 6:
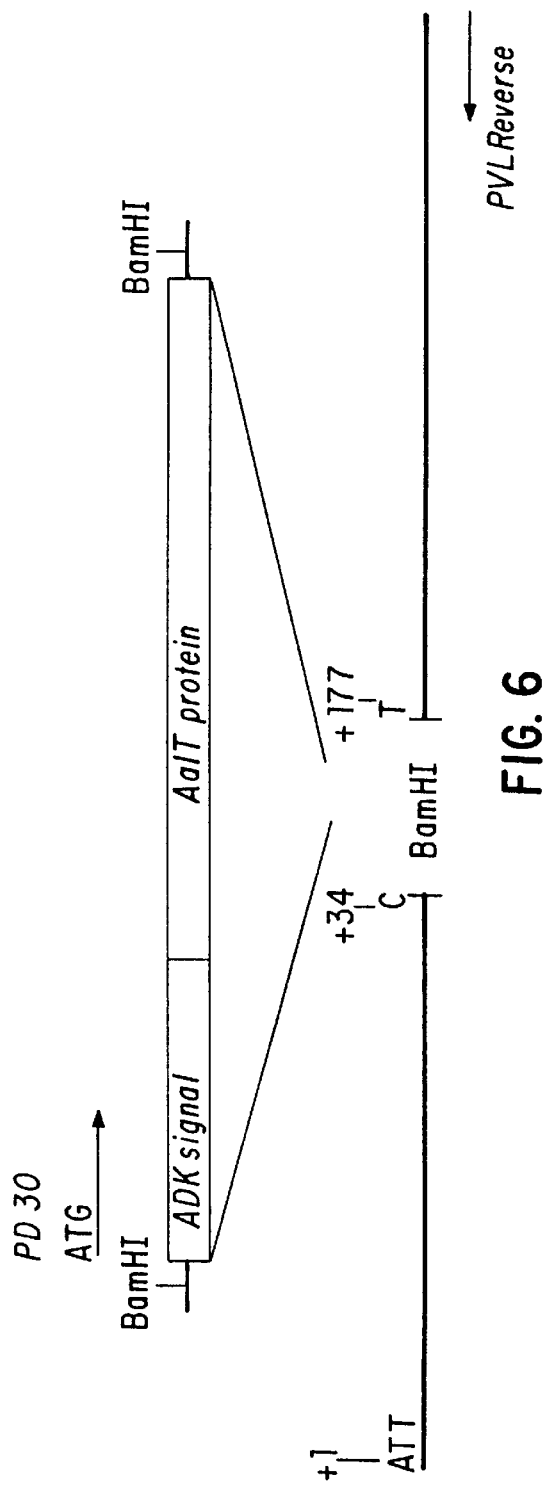
FIG. 6 depicts the polymerase chain reaction (PCR) strategy for the amplification of a adipokinetic hormone gene signal/codon optimized AaIT gene, which is then digested with Bam HI.

To insert the ADK-AaIT gene cassette into pMEV1.1, the ADK-AaIT gene cassette is first recovered from the pVL985/ADK-AaIT transfer vector of Example 12 by PCR. The PCR strategy is shown in FIG. 6. The (+)strand primer used for this reaction is oligonucleotide PD30, whose 5' terminus coincides with the ATG translation initiation codon of the ADK-AaIT gene. The sequence of PD30 is as follows:

```
PD30 5' - ATGTACAAACTGACCGTCTTCCTGATG - 3'
(SEQ ID NO:11)
```

The (−) strand primer in each case is PVLReverse (SEQ ID NO:5) (see Example 10), which hybridizes to a site located 205 to 226 bp downstream of the polyhedrin gene translational start site, or about 35 bases downstream of the site of ADK-AaIT gene insertion in the pVL985/ADK-AaIT template.

For the amplification reaction, 50 pmol of each primer is combined with 250 pg of pVL985/ADK-AaIT template DNA in a 50 µl reaction mixture containing 10 mM Tris-HCl (pH 8.3), 50 mM KCl, 1.5 mM MgCl$_2$, 200 µM dNTPs, 100 µg/ml gelatin and 2.5 units AmpliTaq™ DNA polymerase (Perkin-Elmer Cetus, Norwalk, Conn.). The reaction is the incubated through 25 cycles of 1 minute at 94° C. (denaturation step), 1.5 minutes at 55° C. (annealing step), and 3.0 minutes at 72° C. (extension step). This is followed by a single 7 minute extension at 72° C. The reaction is then terminated by the addition of EDTA to 10 mM and Sarkosyl (sodium N-lauroylsarcosine) to 0.2% (w/v).

The product is extracted once with phenol:chloroform and precipitated with ethanol. After collection the product is treated with the Klenow fragment of E. coli DNA polymerase I in the presence of all four dNTPs to ensure that the PCR product has a blunt 5' terminus. The 3' terminus of the ADK-AaIT toxin gene cassette is then defined by digesting the product with Bam HI, and the ADK-AaIT containing fragment is purified by electrophoresis on a 1.8% agarose gel.

Figure 7:
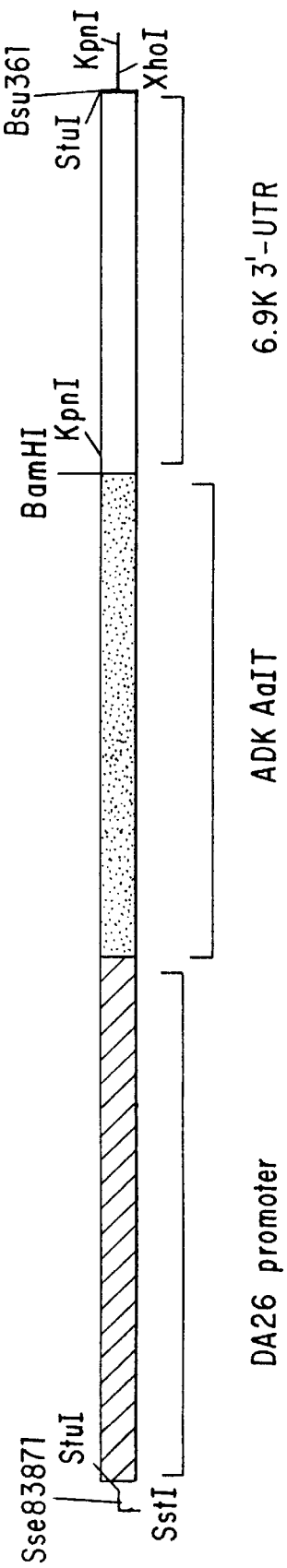
FIG. 7 depicts a schematic representation of a modular expression vector (AC0075.1) formed by inserting the adipokinetic hormone gene signal/codon optimized AaIT into pMEV1.1, which contains the AcMNPV DA26 promoter.

To prepare the pMEV1.1 for toxin gene insertion, the DNA is digested with Esp 3I and the resulting 5' protruding termini are filled in by the action of E. coli DNA polymerase I (Klenow fragment) in the presence of all four dNTPs. The DNA is then digested with Bam HI and the vector is separated from the liberated polylinker fragment by electrophoresis on a 1% low melt agarose gel. The blunt/Bam HI vector fragment is then ligated with an equimolar amount of the blunt/Bam HI ADK-AaIT fragment and transfected into E. coli. The resulting plasmid is designated pMEV1.1/ADK-AaIT-1 (AC0075.1) and contains the ADK-AaIT coding region under the control of the AcMNPV DA26 gene promoter. A schematic representation of the virus insertion module in pMEV1.1/ADK-AaIT-1 (AC0075.1) is presented in FIG. 7.

EXAMPLE 14

Construction of Recombinant Virus V8vEGTDEL-AaIT

To construct a recombinant derivative of V8vEGTDEL containing the ADK-AaIT gene under the control of the AcMNPV DA26 promoter plasmid pMEV1.1/ADK-AaIT-1 is digested with restriction enzymes Bsu 36I and Sse 8387I, and the virus insertion module containing the DA26/ADK-AaIT expression cassette is purified by agarose gel electrophoresis. This fragment is inserted into the Bsu-Sse linker of transfer vector NF4 of Example 10. The resulting transfer vector is designated NF5 and contains the DA26/ADK-AaIT expression cassette positioned 92 bp upstream of the translational start site of the polyhedrin gene, such that the transcriptional polarity of the AaIT gene is opposite that of the polyhedrin gene.

Construction of a recombinant virus containing the AaIT gene is accomplished by co-transfecting Sf9 cells with T-NF002 viral DNA and transfer vector NF5, using procedures described by Summers and Smith (2). Since the T-NF002 virus of Example 9 contains the E. coli lacZ gene in place of the viral polyhedrin gene, recombinants between T-NF002 and the transfer vector NF5 are identified as colorless occlusion-positive plaques when the virus is grown on Sf9 cells in the presence of the chromogenic substrate X-gal. This virus is designated V8vEGTDEL-AaIT and contains the DA26/ADK-AaIT expression cassette positioned 92 bp upstream of a fully functional polyhedrin gene.

EXAMPLE 15

Preparation of V8vEGTDEL-AaIT occlusion bodies

Occlusion bodies (polyhedra) from V8vEGTDEL are formed by infecting Sf9 cells in culture and harvesting the occlusion bodies 5 days post-infection. Briefly, Sf9 cells are maintained at 27° C. in logarithmic growth in spinner cultures at densities of $0.3 \times 10^6$ to $4.0 \times 10^6$ cells per ml in complete TNM-FH medium (prepared as described by Summers and Smith (2)). For occlusion body production the cultures are infected at a density of $1.0 \times 10^6$ cells/ml with V8vEGTDEL-AaIT budded virus at a multiplicity of infection of 0.1–1.0 plaque forming units per cell. After 5 days of incubation at 27° C., intact cells, cell debris and occlusion bodies are collected at 2000 rpm for 10 minutes in a Beckman GPR centrifuge at 4° C. The pellet is resuspended at an equivalent of $10^7$ cells/ml in 50 mM Tris-HCl (pH 7.5)-10 mM EDTA-0.1% (v/v) Triton X-100. Sodium dodecyl sulfate (SDS) is added to a final concentration of 1% (w/v) and the liberated cellular DNA is sheared by vigorous pipeting. The occlusion bodies are collected by centrifugation at 2000 rpm for 10 minutes, washed twice by centrifugation with 50 mM Tris-HCl (pH 7.5)-10 mM EDTA-0.1% Triton X-100 and then resuspended at a density of approximately $10^9$ occlusion bodies per ml in sterile distilled water. The yield is typically in the range of $2 \times 10^{10}$ occlusion bodies per liter of original culture.

REFERENCES

1. Sambrook, J., et al., *Molecular Cloning: A Laboratory Manual,* 2nd ed., Cold Spring Harbor Press, Cold Spring Harbor, N.Y. (1989)
2. Summers, M. D., and Smith, G. E., *A Manual Of Methods For Baculovirus Vectors and Insect Cell Culture Procedures,* Dept. of Entomology, Texas Agricultural Experimental Station and Texas A & M University, College Station, Tex. 77843-2475, Texas Agricultural Experiment Station Bulletin No. 1555 (1987).
3. Casadaban, M. J., et al., *Methods Enzymol.,* 100, 293–303 (1983).
4. Luckow, V. E., and Summers, M. D., *Virology,* 170, 31–39 (1989).
5. Tomalski, M. D., and Miller, L. K., *Nature,* 352, 82–85 (1991).
6. Zlotkin, E., et al., *Toxicon,* 9, 1–8 (1971).
7. Stewart, L. M. D., et al., *Nature,* 352, 85–88 (1991).
8. Maeda, S., *Biochem. Biophys. Res. Commun.,* 165, 1177–1183 (1989).
9. Hammock, B. D., et al., *Nature,* 344, 458–461 (1990).
10. O'Reilly, D. R., et al., *J. Gen. Virology,* 71, 1029–1037 (1990).
11. Wilson, M. E., et al., *J. Virology,* 61, 661–666 (1991).

I claim:

1. An aqueous process for the preparation of a coated pesticidal agent which process comprises:
   a) preparing an aqueous mixture of a pH-dependent polymer and optionally a plasticizer;
   b) dissolving the pH-dependent polymer by adjusting the pH of the mixture of step (a) with a base to a pH above the solubilization pH of the pH dependent polymer;
   c) adding a pesticidal agent, an ultraviolet protector, optionally a stilbene compound, optionally a disintegrating agent and optionally a glidant to the solution of step (b), and blending to produce a homogeneous suspension containing dissolved pH-dependent polymer;
   d) drying the homogeneous suspension of step (c); and optionally
   e) milling the dried material of step (d),
wherein said pH dependent polymer is selected from the group consisting of methacrylic acid and methyl methacrylate copolymers, maleic anhydride and styrene copolymers, and mixtures thereof.

2. The process according to claim 1 wherein the pH-dependent polymer is selected from the group consisting of a methacrylic acid and methyl methacrylate copolymer, a mixture of methacrylic acid and methyl methacrylate copolymers and a maleic anhydride and styrene copolymer; the plasticizer is selected from the group consisting of a polyethylene glycol, a polypropylene glycol, diethyl phthalate, dibutyl phthalate, a citric acid ester, castor oil and triacetin; the base is selected from the group consisting of ammonium hydroxide, an alkali metal hydroxide and an alkaline earth metal hydroxide; the pesticidal agent is an insecticidal pathogen; the ultraviolet protector is selected from the group consisting of carbon black, a benzophenone, a dye and titanium dioxide; the pH is adjusted in step (b) to pH 8.5 to 10; the disintegrating agent is selected from the group consisting of (a) salts of the condensation products of formaldehyde with the sulfonation products of polycyclic aromatic compounds, (b) a hydrophilic starch, (c) carboxy methylcellulose and (d) polyvinyl pyrrolidine; and the glidant is selected from the group consisting of talc, magnesium stearate, calcium stearate and calcium sulfate.

3. The process according to claim 2 wherein the plasticizer is a polyethylene glycol having a molecular weight of about 300 to 1,000; the base is ammonium hydroxide; the insecticidal pathogen is a virus; the disintegrating agent is a sodium sulfonate of a naphthalene formaldehyde condensate; and the glidant is talc.

4. The process according to claim 3 wherein the virus is selected from the group consisting of wild gypsy moth NPV, AcMNPV E2, AcMNPV L1, AcMNPV V8, V8vEGTDEL, V8vEGTDEL-AaIT and *Heliothis zea* NPV.

5. The process according the claim 1 wherein the coated pesticidal agent has a particle size less than about 20 $\mu$m.

6. The process according to claim 5 wherein the coated pesticidal agent has a particle size of about 2 $\mu$m to 10 $\mu$m.

7. The process according to claim 1 wherein the homogeneous suspension is air dried or spray dried.

8. The process according to claim 1 wherein the coated pesticidal agent comprises a pesticidal agent core surrounded by a matrix which comprises about 2 to 25% by weight of the pH-dependent polymer, 0% to about 5% by weight of the plasticizer, about 5 to 45% by weight of the ultraviolet protector, 0% to about 75% by weight of the stilbene compound, 0% to about 10% by weight of the disintegrating agent, and 0% to about 10% by weight of the glidant.

9. The process according to claim 8 wherein the ratio by weight of the pesticidal agent to the matrix is about 1:1 to 1:10.

10. A process for the preparation of a coated pesticidal agent which process comprises:

a) blending a mixture of a pH-dependent polymer, a pesticidal agent, optionally a plasticizer, an ultraviolet protector, optionally a stilbene compound, optionally a disintegrating agent and optionally a glidant in an organic solvent selected from the group consisting of acetone, a $C_1$–$C_3$ alcohol, and mixtures thereof;

b) drying the homogeneous suspension of step (a); and optionally c) milling the dried material of step (b), wherein said pH dependent polymer is selected from the group consisting of methacrylic acid and methyl methacrylate copolymers, maleic anhydride and styrene copolymers, and mixtures thereof.

11. The process according to claim 10 wherein the organic solvent is a mixture of acetone and a $C_1$–$C_3$alcohol and the ratio by weight of acetone to the $C_1$–$C_3$alcohol is about 1:9 to 9:1.

12. The process according to claim 11 wherein the ratio by weight is about 1.4 to 2:3.

13. The process according to claim 10 wherein the pH-dependent polymer is selected from the group consisting of a methacrylic acid and methyl methacrylate copolymer, a mixture of methacrylic acid and methyl methacrylate copolymers and a maleic anhydride and styrene copolymer; the pesticidal agent is an insecticidal pathogen; the plasticizer is selected from the group consisting of a polyethylene glycol, a polypropylene glycol, diethyl phthalate, dibutyl phthalate, a citric acid ester, castor oil and triacetin; the ultraviolet protector is selected from the group consisting of carbon black, a benzophenone, a dye and titanium dioxide; the disintegrating agent is selected from the group consisting of (a) salts of the condensation products of formaldehyde with the sulfonation products of polycyclic aromatic compounds, (b) a hydrophilic starch, (c) carboxymethyl cellulose and (d) polyvinyl pyrrolidine; the glidant is selected from the group consisting of talc, magnesium stearate, calcium stearate and calcium sulfate; and the $C_1$–$C_3$alcohol is isopropanol.

14. The process according to claim 13 wherein the pesticidal agent is a virus selected from the group consisting of wild gypsy moth NPV, AcMNPV E2, AcMNPV L1, AcMNPV V8, V8vEGTDEL, V8vEGTDEL-AaIT and *Heliothis zea* NPV.

15. A coated pesticidal agent which comprises a pesticidal agent core surrounded by a matrix which comprises about 2 to 25% by weight of a pH-dependent polymer selected from the group consisting of methacrylic acid and methyl methacrylate copolymers, maleic anhydride and styrene copolymers, and mixtures thereof, 0% to about 5% by weight of a plasticizer, about 5 to 45% by weight of an ultraviolet protector, 0% to about 75% by weight of a stilbene compound, 0% to about 10% by weight of a disintegrating agent, and 0% to about 10% by weight of a glidant.

16. The coated pesticidal agent according to claim 15 wherein the ratio by weight of the pesticidal agent to the matrix is about 1:1 to 1:10.

17. The coated pesticidal agent according to claim 15 which comprises about 2 to 20% by weight of the pH-dependent polymer, 0% to about 3% by weight of the plasticizer, about 5% to 35% by weight of the ultraviolet protector, and about 25 to 75% by weight of the stilbene compound.

18. The coated pesticidal agent according to claim 15 wherein the pesticidal agent is an insecticidal pathogen; the plasticizer is selected from the group consisting of a polyethylene glycol, a polypropylene glycol, diethyl phthalate, dibutyl phthalate, a citric acid ester, castor oil and triacetin; the ultraviolet protector is selected from the group consisting of carbon black, a benzophenone, a dye and titanium dioxide; the disintegrating agent is selected from the group consisting of (a) salts of the condensation products of formaldehyde with the sulfonation products of polycyclic aromatic compounds, (b) a hydrophilic starch, (c) carboxy methyl-cellulose and (d) polyvinyl pyrrolidine; and the glidant is selected from the group consisting of talc, magnesium stearate, calcium stearate and calcium sulfate.

19. The coated pesticidal agent according to claim 18 wherein the insecticidal pathogen is a virus; the plasticizer is a polyethylene glycol having a molecular weight of about 300 to 1,000; the stilbene compound is selected from the group consisting of Blancophor BBH, Calcofluor White M2R and Phorwite AR; the disintegrating agent is a sodium sulfonate of a naphthalene formaldehyde condensate; and the glidant is talc.

20. The coated pesticidal agent according to claim 19 wherein the virus is selected from the group consisting of wild gypsy moth NPV, AcMNPV E2, AcMNPV L1, AcMNPV V8, V8vEGTDEL; V8vEGTDEL-AaIT and *Heliothis zea* NPV.

21. The coated pesticidal agent according to claim 20 having a particle size of less than 20 μm.

22. The coated pesticidal agent according to claim 21 having a particle size of about 2 μm to 10 μm.

23. A wettable powder pesticidal composition which comprises about 2% to 25% by weight of a wetting agent; about 2 to 40% by weight of a dispersing agent; about 10 to 70% by weight of a bulking agent; about 1 to 10% by weight of a flow enhancing agent; 0% to about 20% by weight of a pH-modifying agent; and about 5 to 75% by weight of a coated pesticidal agent which comprises a pesticidal agent core surrounded by a matrix which comprises about 2 to 25% by weight of a pH-dependent polymer, selected from the group consisting of methacrylic acid and methyl methacrylate copolymers, maleic anhydride and styrene copolymers, and mixtures thereof, 0% to about 5% by weight of a plasticizer, about 5 to 45% by weight of an ultraviolet protector, 0% to about 75% by weight of a stilbene compound, 0% to about 10% by weight of a disintegrating agent, and 0% to about 10% by weight of a glidant.

24. The wettable powder pesticidal composition according to claim 23 wherein the coated pesticidal agent has a particle size of less than about 20 μm.

* * * * *